US006471648B1

United States Patent
Gamelsky et al.

(10) Patent No.: US 6,471,648 B1
(45) Date of Patent: Oct. 29, 2002

(54) MEDICAL DIAGNOSTIC ULTRASOUND IMAGING SYSTEM WITH A ROTATABLE USER INTERFACE ELEMENT HAVING A NON-ROTATABLE INDICATOR

(75) Inventors: Jeff N. Gamelsky, Palo Alto, CA (US); Richard Henderson, Fremont, CA (US); Glenn Hansen, San Jose, CA (US)

(73) Assignee: Acuson Corporation, Mountain View, CA (US)

( * ) Notice: Subject to any disclaimer, the term of this patent is extended or adjusted under 35 U.S.C. 154(b) by 59 days.

(21) Appl. No.: 09/617,076

(22) Filed: Jul. 17, 2000

(51) Int. Cl.[7] .................................................. A61B 8/00
(52) U.S. Cl. .......................................... 600/437; 362/26
(58) Field of Search ............................ 600/437; 362/23, 362/26; 128/903; 116/298, 202, 28; 200/316

(56) References Cited

U.S. PATENT DOCUMENTS

| | | | | |
|---|---|---|---|---|
| 4,646,206 A | * | 2/1987 | Bauer et al. | 116/28 R |
| 5,093,764 A | * | 3/1992 | Hasegawa et al. | 116/202 |
| 5,335,148 A | | 8/1994 | Tominaga | |
| 5,710,545 A | * | 1/1998 | Dunn | 116/298 |
| 5,752,759 A | | 5/1998 | Pizzo | |
| 5,913,414 A | * | 6/1999 | Pollock et al. | 200/316 |
| 6,019,478 A | * | 2/2000 | Pizzo | 362/26 |
| 6,176,589 B1 | * | 1/2001 | Ishiguro | 362/23 |
| 6,238,344 B1 | * | 5/2001 | Gamelsky et al. | 128/903 |

OTHER PUBLICATIONS

"Acuson 128 XP Computed Sonography System" Manual, pp. 3–20 (1988).
"Acuson Sequoia 512 Ultrasound System" Manual, cover page (1996).
Toshiba's "Operation Manual [Fundamentals] for Diagnostic Ultrasound System Model SSH–140A (2B730–474E*H)," p. 4–3 (1992).

* cited by examiner

*Primary Examiner*—Marvin M. Lateef
*Assistant Examiner*—Ruby Jain

(57) ABSTRACT

The preferred embodiments described herein provide a medical diagnostic ultrasound imaging system with a rotatable user interface element having a non-rotatable indicator. In one preferred embodiment, a medical diagnostic ultrasound imaging system user interface is provided with a user interface element comprising a rotatable portion disposed around a non-rotatable portion that comprises an indicator identifying a function of the user interface element. With this preferred embodiment, the indicator does not rotate with rotation of the rotatable portion. In another preferred embodiment, a medical diagnostic ultrasound imaging system is provided with a user interface comprising a rotary input device comprising a rotatable shaft, an inner member disposed around and fixed with respect to the rotatable shaft, and an outer member disposed around the inner member and coupled with the rotatable shaft. The inner member comprises an indicator identifying a function of the rotary input device, and rotation of the outer member rotates the rotatable shaft of the rotary input device without rotating the inner member.

24 Claims, 3 Drawing Sheets

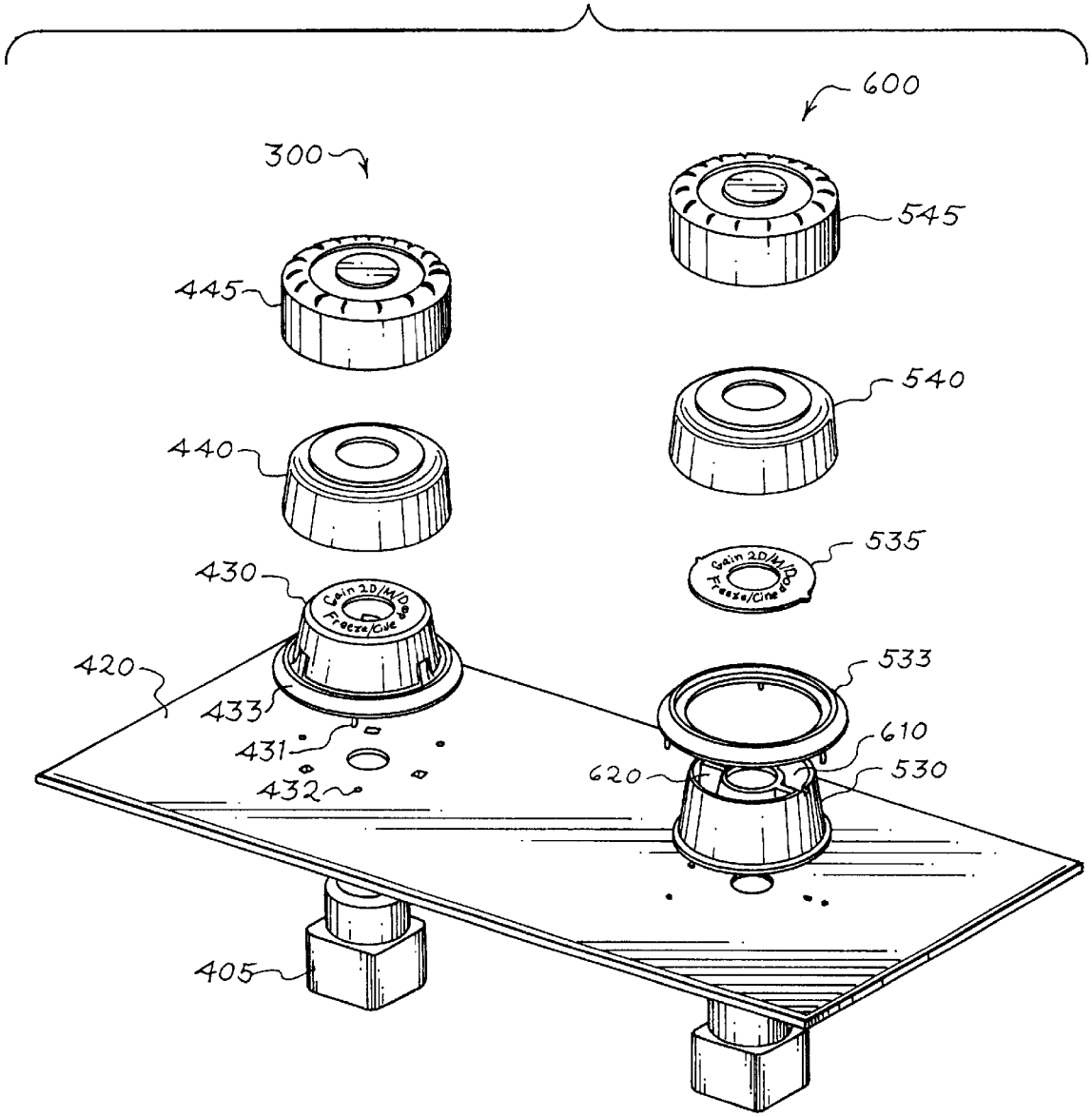

MEDICAL DIAGNOSTIC ULTRASOUND IMAGING SYSTEM WITH A ROTATABLE USER INTERFACE ELEMENT HAVING A NON-ROTATABLE INDICATOR

BACKGROUND

Medical diagnostic ultrasound imaging systems often have a user interface with several different types of user interface elements (e.g., buttons or knobs) that affect one or more functions of the ultrasound system (e.g., gain). While buttons can have text printed on their face to describe their function, knobs often do not because text printed on the face of the knob would be difficult to read as the knob is rotated. Accordingly, many ultrasound system have text printed on a separate label or overlay adjacent to the knob on the user interface. In some systems, the text is back-lit to allow a user to read the text in a dim room, and the knob itself may be illuminated to assist the user in locating the knob. When a knob is associated with multiple functions, several adjacent labels can be used to describe each of these functions, and these labels can be selectively illuminated to provide an indication of which function is currently active. Under some lighting conditions (especially if the text is lit and the knob is not lit), the text adjacent the knob may not be easily discerned due to the proximity of the text to the knob.

SUMMARY

The present invention is defined by the following claims, and nothing in this section should be taken as a limitation on those claims.

By way of introduction, the preferred embodiments described below provide a medical diagnostic ultrasound imaging system with a rotatable user interface element having a non-rotatable indicator. In one preferred embodiment, a medical diagnostic ultrasound imaging system user interface is provided with a user interface element comprising a rotatable portion disposed around a non-rotatable portion that comprises an indicator identifying a function of the user interface element. With this preferred embodiment, the indicator does not rotate with rotation of the rotatable portion. In another preferred embodiment, a medical diagnostic ultrasound imaging system is provided with a user interface comprising a rotary input device comprising a rotatable shaft, an inner member disposed around and fixed with respect to the rotatable shaft, and an outer member disposed around the inner member and coupled with the rotatable shaft. The inner member comprises an indicator identifying a function of the rotary input device, and rotation of the outer member rotates the rotatable shaft of the rotary input device without rotating the inner member.

The preferred embodiments will now be described with reference to the attached drawings.

BRIEF DESCRIPTION OF THE DRAWINGS

FIG. 5 is an illustration of two knobs of a medical diagnostic ultrasound imaging system user interface of a preferred embodiment.

DETAILED DESCRIPTION OF THE PRESENTLY PREFERRED EMBODIMENTS

Figure 1:
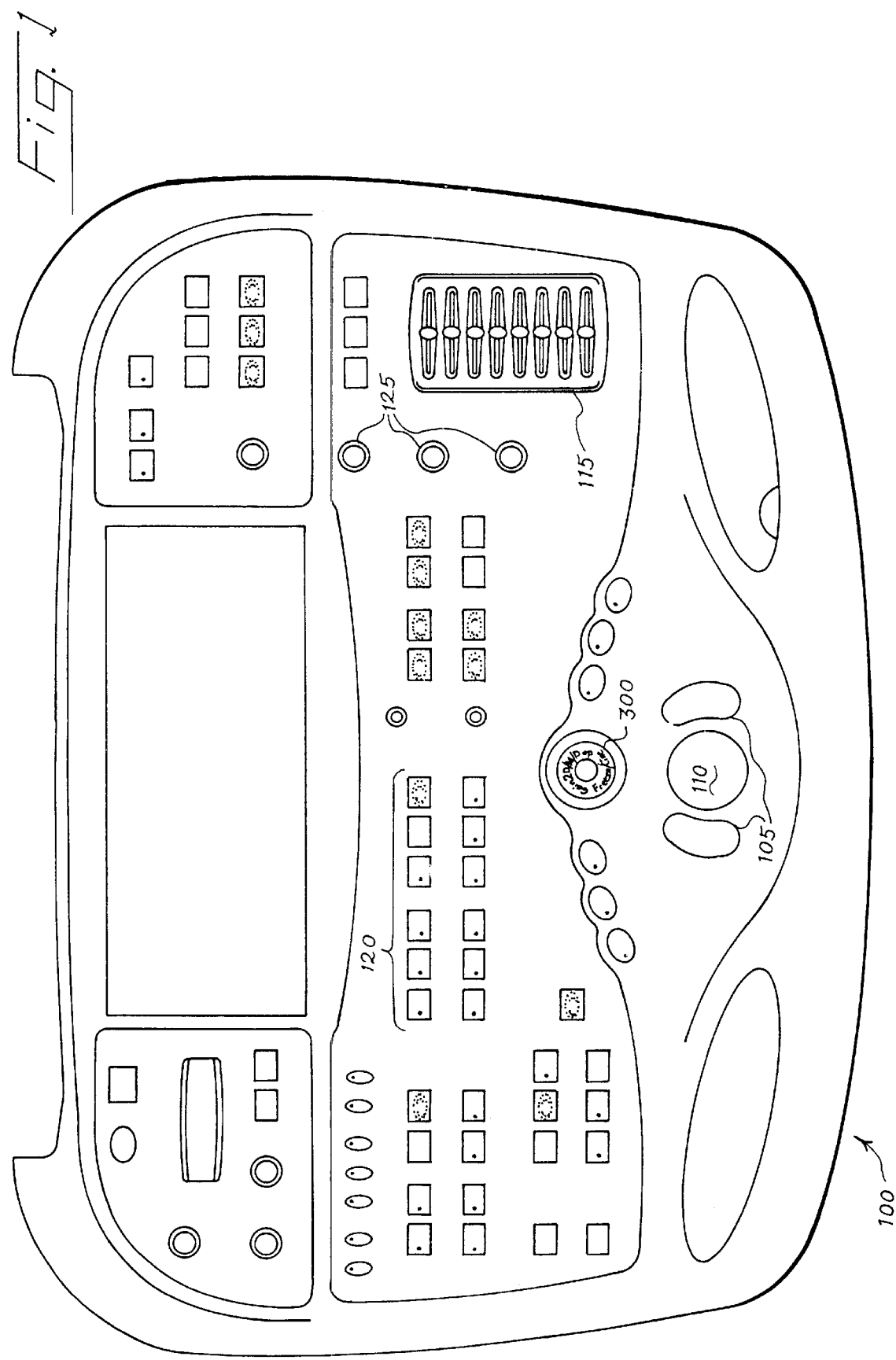
FIG. 1 is an illustration of a medical diagnostic ultrasound imaging system user interface of a preferred embodiment.

Turning now to the drawings, FIG. 1 is an illustration of a medical diagnostic ultrasound imaging system user interface 100 of a preferred embodiment. The user interface 100 comprises a number of user interface elements: select switches 105, a trackball 110, slides 115, buttons 120, and knobs 125. The user interface 100 also comprises a knob 300 with non-rotating text, which will be described in more detail below. The user interface 100 can comprise additional user interface elements.

Figure 2:
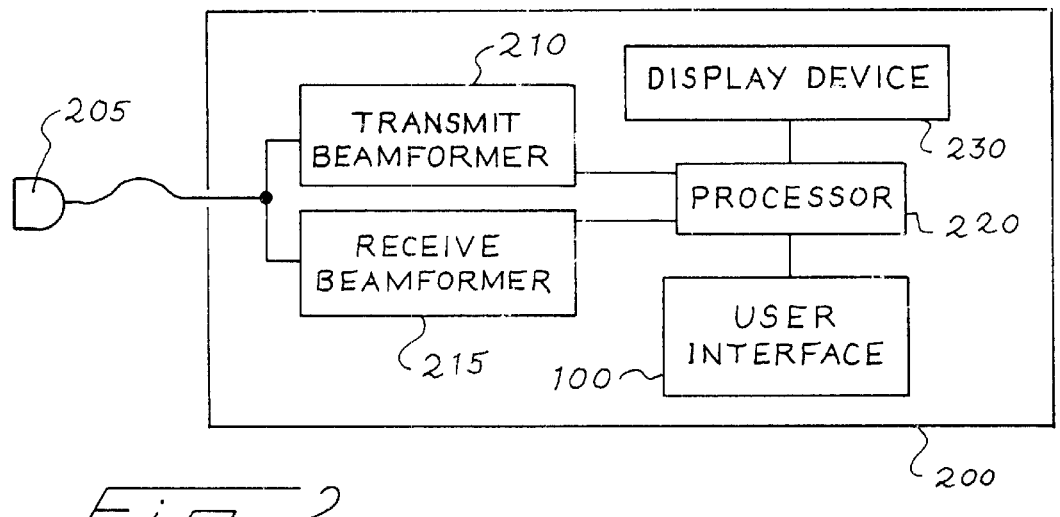
FIG. 2 is a block diagram of a medical diagnostic ultrasound imaging system of a preferred embodiment.

As shown in FIG. 2, the user interface 100 is part of a medical diagnostic ultrasound imaging system 200. The ultrasound system 200 can be used with any suitable imaging mode (e.g., B-mode imaging, Doppler imaging, tissue harmonic imaging, contrast agent harmonic imaging, etc.) and with any suitable transducer 205 (e.g., 1D, 1.5D, planoconcave, single element, phased-array, etc.). The transducer 205 is coupled with a transmit beamformer 210 and a receive beamformer 215. As used herein, the term "coupled with" means directly coupled with or indirectly coupled with through one or more components. The beamformers 210, 215 are each coupled with a processor 220, which is coupled with the user interface 100 and a display 230. The processor 220 can be separate from or combined with (in part or in whole) other processors of the ultrasound system 200 (including attendant processors), which are not shown in FIG. 2 for simplicity.

In operation, the processor 220, which includes any appropriate hardware (analog or digital) and/or software components, causes the transmit beamformer 210 to apply a voltage to the transducer 205 to cause it to vibrate and emit an ultrasonic beam into an object, such as human tissue (i.e., a patient's body). Ultrasonic energy reflected from the body impinges on the transducer 205, and the resulting voltages created by the transducer 205 are received by the receive beamformer 215. The processor 220 processes the sensed voltages to create an ultrasound image associated with the reflected signals and displays the image on the display 230. The user interface 100 can be used to control functions of the ultrasound imaging system. For example, the user interface 100 can be used to adjust parameters used in the transmit, receive, display, and image storage operations.

Figure 3:
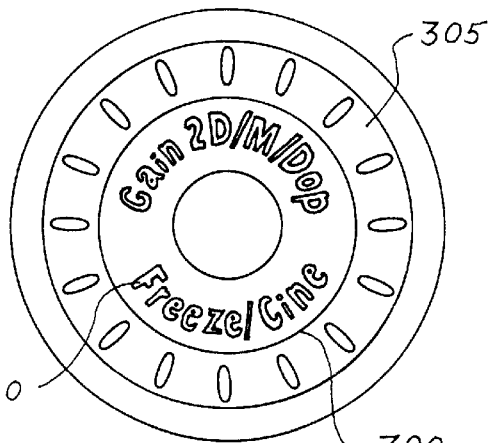
FIG. 3 is an illustration of a knob of a medical diagnostic ultrasound imaging system user interface of a preferred embodiment.

Turning again to the drawings, FIG. 3 is an illustration of knob 300 of the ultrasound imaging system user interface 100 of FIG. 1. This knob 300 comprises a rotatable portion 305 disposed around a non-rotatable portion 310. The non-rotatable portion 310 comprises an indicator identifying at least one function of the knob 300. As used herein, the term "indicator" broadly refers to any visual that can be used to provide an indication of function. Merely by way of example, an indicator can take the form of text and/or a graphic, such as an icon, symbol, color, or shape. In the knob 300 of FIG. 3, the indicator takes the form of text ("Gain 2D/M/Dop Freeze/Cine"). Because the non-rotatable portion 310 does not rotate when the rotatable portion 305 is rotated, the indicator on the non-rotatable portion 310 remains in a fixed position with respect to the rotatable portion 305. Because the indicator does not rotate with the rotatable portion 305, the indicator is easily read even when the knob 300 is rotated. Accordingly, when the indicator takes the form of text, the text is legible regardless of the knob's 300 rotational position. Further, providing the indicator directly on the knob 300 instead of adjacent to the knob 300 creates a logical association between the text and knob 300, making the functionality of the knob 300 more apparent and making the knob easy to find on the user interface 100. Additionally, placing the text on the knob 300 consumes less console area and provides a more consistent user interface design in user interfaces having buttons with text printed on their face to describe their functionality.

Figure 4:
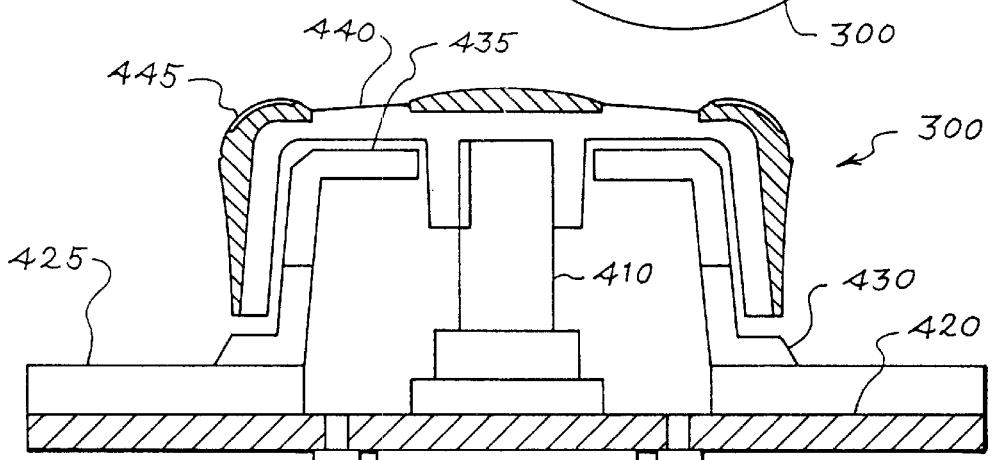
FIG. 4 is a sectional view of a knob of a medical diagnostic ultrasound imaging system user interface of a preferred embodiment.

FIG. 4 is a cross-sectional view of the knob 300 of FIG. 3. As shown in FIG. 4, the user interface comprises a rotary input device 405 comprising a rotatable shaft 410. The rotary input device 405 is attached to a printed circuit board 420, which is disposed under a bezel 425 of the user interface. The rotatable shaft 410 extends through the printed circuit board 420 and the bezel 425. In operation, rotation of the rotatable shaft 410 results in a signal applied to the ultrasound system's processor 220 via the printed circuit board 420 to affect, for example, parameters used in the transmit, receive, and/or display operations of the ultrasound system 200. In one preferred embodiment, the rotary input device 405 takes the form of a switch device in which the rotatable shaft 410 is also axially movable along its rotational axis. Axial movement of the rotatable shaft 410 (i.e., pressing the rotatable shaft 410) triggers a switch, thereby providing an additional user input.

Disposed around the rotatable shaft 410 is an inner member 430, which is fixed with respect to the rotatable shaft 410. The inner member 430 comprises an indicator that identifies at least one function of the rotary input device 405. The indicator can be printed directly on or applied as a label to the inner member 430. Alternatively, the inner member 430 can comprise an inner cap 435, which is fitted over or integral with the inner member 430, as shown in FIG. 4. An outer member 440 is disposed around the inner member 430 and is coupled with the rotatable shaft 410. As shown in FIG. 4, the top portion of the rotatable shaft 410 is tapered to fit into a corresponding tapered portion of the outer member 440. Preferably, at least the top surface of the outer member 440 is transparent to allow a user to see the indicator on the inner member 430. Disposed over the outer member 410 is an overmolded grip 445. The overmolded grip 445 has undulations spaced about its periphery to allow a user to firmly grasp and rotate the knob 300. In this preferred embodiment, the overmolded grip 445 is a separate opaque component that is attached or snapped on to the outer member 440. In an alternate embodiment, the grip 445 is integral with the outer member 440, such as when the outer member 440 is textured to create a grip surface. Because the inner member 430 is fixed with respect to the rotatable shaft 410, rotation of the outer member 440 rotates the rotatable shaft 410 without rotating the inner member 430. In this way, the indicator of the inner member 430 retains its position even when the knob 300 is rotated. Accordingly, when the indicator takes the form of text, rotation of the knob 300 does not cause rotation of the text, and the text is legible at any knob position.

In the preferred embodiment shown in FIG. 4, a light source 450 is positioned under the inner member 430 to illuminate the indicator, thereby backlighting the text "Gain 2D/M/Dop Freeze/Cine", The light source 450 also illuminates an illumination ring (such as a frosted acrylic or polycarbonate ring) disposed around or integral with the inner member 430, which can be used to light the exterior of the knob 300. When a light source 450 is used, it is preferred that the inner cap 435 (or the top surface of the inner member 430 itself) be transparent or translucent. The light source 450 can be surface mounted or through-hole and take any suitable form, including, but not limited to an LED or an incandescent or fluorescent light source. In addition to backlighting the indicator, the light source 450 can be used to indicate whether or not the knob 300 is active. For example, the light source 450 can be turned on or off when the functionality of the knob 300 is active or inactive, respectively. In one preferred embodiment, pressing the knob 300 provides axial movement of the rotatable shaft 410, which toggles the knob 300 into an active state and turns the light source 450 on, thereby alerting the user that the knob 300 is active. By pressing the knob 300 again, the knob 300 is toggled back to an inactive state, and the light source 450 turns off. As described in more detail below, the light source can also be used to indicate different functions of the knob 300 in addition to merely indicating whether the knob 300 is active or inactive.

In one preferred embodiment, the rotary input device 405 takes the form of a potentiometer or an optical or mechanical encoder. A suitable potentiometer or encoder can be purchased from manufacturers such as Oak or Bourns. It is preferred that the inner cap 435 (or the top surface of the inner member 430) be made of a clear or translucent material (such as polycarbonate), which can be frosted or textured to diffuse light. It is also preferred that at least the top surface of the outer member 440 be made from a clear material, such as a clear acrylic, polycarbonate, or other material that allows the indicator of the inner member 430 to be viewed through the outer member 440. Preferably, the overmolded grip 445 is an opaque elastomeric such as Santoprene. In an alternate embodiment, the overmolded grip 445 is a clear component, so that the knob itself is completely transparent. It is also preferred that the illumination ring be a frosted acrylic or polycarbonate ring. Any suitable knob size can be used (e.g., ¾" to 1½").

FIG. 5 shows the construction of the knob 300 of FIG. 4. For simplicity, the rotatable shaft 410 of the rotary member 405, the bezel 425, and the light source 450 are not shown in FIG. 5. As shown in FIG. 5, a protrusion 431 on the inner member 430 snap fits into a recess 432 formed in the printed circuit board 420 (or in the bezel) to fix the inner member 430 with respect to the rotatable shaft. In this preferred embodiment, the indicator (text) is printed directly on the top surface of the inner member 430, and an illumination ring 433 is disposed around the inner member 430. To construct the knob 300, the outer member 440 is placed over the inner member 430, and the overmolded grip 445 is placed over the outer member 440. In this preferred embodiment, the components of the knob 300 snap-fit together for ease of assembly.

FIG. 5 also shows the construction of a knob 600 of another preferred embodiment. Construction of knob 600 is similar to that of knob 300 in that an outer member 540 is placed over the inner member 530, followed by the overmolded grip 545. In this preferred embodiment, however, the illumination ring 533 and the inner cap 535 are separate components from the inner member 530. Additionally, the inner member 530 of this preferred embodiment defines a plurality of chambers (here, chambers 610 and 620) created by an opaque partition. The chambers 610, 620 are positioned such that each chamber 610, 620 is disposed under a different indicator. In the embodiment of FIG. 5, chamber 610 is positioned under the text "Gain 2D/M/Dop", and chamber 620 is positioned under the text "Freeze/Cine", A light source (not shown) is positioned in each chamber 610, 620.

In this embodiment, the light sources in each chamber 610, 620 can be activated independently to provide selective lighting of the indicators. For example, in this preferred embodiment, the knob 600 is associated with two different functions: changing the gain ("Gain 2D/M/Dop") and changing the display of a Cine loop ("Freeze/Cine"). The knob 600 affects gain when the ultrasound system is in an imaging mode and affects loop display when the ultrasound system is in an image review mode. When none of the light sources is lit, the knob 600 is inactive (i.e., rotation of the knob 600 will not affect the ultrasound system). If the user presses the knob 600, the knob 600 is toggled into an active mode. In the embodiment described above that did not contain selective lighting, toggling the knob 300 into the active mode resulted in the light source 450 turning on, thereby backlighting the indicator of the inner member 430 (i.e., "Gain 2D/M/Dop Freeze/Cine"). In that embodiment, the "indicator" was the entire text phrase "Gain 2D/M/Dop Freeze/Cine." In the present embodiment, instead of lighting the entire text phrase, the text phrase is divided into two indicators ("Gain 2D/M/Dop" and "Freeze/Cine"), and only the indicator that is associated with the active function is lit. For example, if the knob 600 is activated when the ultrasound system is in an imaging mode, only the light source in chamber 610 will light so that "Gain 2D/M/Dop" will be backlit while "Freeze/Cine" will not. This informs the user that only the gain function is available.

In a presently preferred embodiment, multiple light sources with different light characteristic (e.g., colors or light intensity) or a single light source that can provide different light characteristic is used in each chamber to indicate the state of the indicated function. In this way, different lighting states will indicate different states of the knob's functions. For example, if the knob 600 is activated when the ultrasound system is in an imaging mode, a white light can be lit in chamber 610 to indicate that the "Gain 2D/M/Dop" function is available and active, while a yellow light can be lit in chamber 620 to indicate that the "Freeze/Cine" is available but not active. Further, while only two chambers 610, 620 are shown in FIG. 5, it should be noted that additional chambers can be used. For example, the single indicator "Gain 2D/M/Dop" can be divided into three separate indicators "Gain 2D", "M", and "Dop", each with its own chamber and light source.

It is important to note that any of the various aspects of any of the preferred embodiments can be used alone or in combination. For example, in one embodiment, an inner member can be fixed with or without having multiple chambers to provide selective lighting of an indicator. Additionally, it should be noted that the alternatives described above are only some of the various alternatives that can be employed with these preferred embodiments. For example, although the preferred embodiments were discussed above in terms of a "knob," the preferred embodiments can be applied to any suitable user interface element.

It is intended that the foregoing detailed description be understood as an illustration of selected forms that the invention can take and not as a definition of the invention. It is only the following claims, including all equivalents, that are intended to define the scope of this invention.

What is claimed is:

1. In a medical diagnostic ultrasound imaging system comprising a transmit beamformer, a receive beamformer, a processor coupled with the transmit and receive beamformers, and a user interface coupled with the processor, the user interface controlling a function of the ultrasound imaging system, the improvement comprising:

wherein the user interface comprises:
 a rotary input device comprising a rotatable shaft;
 an inner member disposed around and fixed with respect to the rotatable shaft and comprising an indicator identifying a function of the rotary input device; and
 an outer member disposed around the inner member and coupled with the rotatable shaft, whereby rotation of the outer member rotates the rotatable shaft of the rotary input device without rotating the inner member.

2. The invention of claim 1, wherein the indicator is provided on a top surface of the inner member.

3. The invention of claim 1 further comprising a grip member disposed around the outer member.

4. The invention of claim 1, wherein a grip portion is formed in the outer member.

5. The invention of claim 1 further comprising a light source positioned to illuminate the indicator.

6. The invention of claim 5, wherein the rotatable shaft is axially movable along its rotational axis, and wherein axial movement activates the light source.

7. The invention of claim 1, wherein the inner member defines a plurality of chambers, and wherein the invention further comprises a plurality of light sources, each light source of the plurality of light sources being positioned to illuminate respective chambers of the plurality of chambers.

8. The invention of claim 7, wherein an additional light source is positioned to illuminate one of the plurality of chambers with light of a different characteristic from the first-mentioned light source.

9. The invention of claim 7, wherein at least one of the plurality of light sources is operative to provide at least two different light characteristics.

10. The invention of claim 7, wherein the inner member comprises at least one additional indicator, and wherein the first-mentioned indicator and the at least one additional indicator are positioned over respective chambers of the plurality of chambers.

11. The invention of claim 10, wherein at least some of the light sources are activated independently to provide selective lighting of the indicators.

12. The invention of claim 1 further comprising an illumination ring disposed around the inner member.

13. A medical diagnostic ultrasound imaging system user interface comprising:

a user interface controlling a function of an ultrasound imaging system, the user interface element comprising a rotatable portion disposed around a non-rotatable portion comprising an indicator identifying a function of the user interface element, whereby the indicator of the non-rotatable portion does not rotate with rotation of the rotatable portion.

14. The invention of claim 13 further comprising a light source positioned to illuminate the indicator.

15. The invention of claim 13, wherein the user interface element defines a plurality of chambers, and wherein the invention further comprises a plurality of light sources, each light source of the plurality of light sources being positioned to illuminate respective chambers of the plurality of chambers.

16. The invention of claim 15, wherein the non-rotatable portion comprises at least one additional indicator, and wherein the first-mentioned indicator and the at least one additional indicator are positioned over respective chambers of the plurality of chambers.

17. The invention of claim 16, wherein at least some of the light sources are activated independently to provide selective lighting of the indicators.

18. The invention of claim 15 further comprising an additional light source positioned to illuminate one of the plurality of chambers with light of a different characteristic from the first-mentioned light source.

19. The invention of claim 13, wherein the user interface element comprises a knob.

20. In a medical diagnostic ultrasound imaging system comprising a transmit beamformer, a receive beamformer, a processor coupled with the transmit and receive beamformers, and a user interface coupled with the processor, the user interface controlling a function of the ultrasound imaging system, the improvement comprising:

the user interface comprising:
  a rotary input device comprising a rotatable shaft;
  an inner member disposed around and fixed with respect to the rotatable shaft and comprising an indicator identifying a function of the rotary input device, wherein the inner member comprises an inner cap, and wherein the indicator is provided on the inner cap;
  an outer member disposed around the inner member and coupled with the rotatable shaft, whereby rotation of the outer member rotates the rotatable shaft of the rotary input device without rotating the inner member.

21. In a medical diagnostic ultrasound imaging system comprising a transmit beamformer, a receive beamformer, a processor coupled with the transmit and receive beamformers, and a user interface coupled with the processor, the user interface controlling a function of the ultrasound imaging system, the improvement comprising:

the user interface comprising:
  a rotary input device comprising a rotatable shaft;
  an inner member disposed around and fixed with respect to the rotatable shaft and comprising an indicator identifying a function of the rotary input device;
  an outer member disposed around the inner member and coupled with the rotatable shaft, whereby rotation of the outer member rotates the rotatable shaft of the rotary input device without rotating the inner member; and
  at least one light source positioned to illuminate the indicator and operative to provide different light characteristics to indicate a state of the function identified by the indicator, wherein a first light characteristic indicates that the function identified by the indicator is active and wherein a second light characteristic indicates that the function identified by the indicator is available but not active.

22. The invention of claim 21, wherein the at least one light source indicates that the function identified by the indicator is off by not illuminating the indicator.

23. The invention of claim 21, wherein the at least one light source comprises a single light source that provides the different light characteristics.

24. The invention of claim 21, wherein the at least one light source comprises a plurality of light sources, each providing a respective light characteristic.

* * * * *